United States Patent [19]

Borzelli et al.

[11] 4,307,027

[45] Dec. 22, 1981

[54] CONTINUOUS PROCESS FOR PREPARING DRY METALLIC SALTS OF HIGHER FATTY ACIDS

[75] Inventors: Richard D. Borzelli, Bayonne; Joseph Cunder, Short Hills, both of N.J.

[73] Assignee: Dart Industries Inc., Los Angeles, Calif.

[21] Appl. No.: 129,124

[22] Filed: Mar. 10, 1980

Related U.S. Application Data

[63] Continuation of Ser. No. 28,009, Apr. 9, 1979, abandoned.

[51] Int. Cl.$^3$ ............................................. C08H 17/36
[52] U.S. Cl. .................................. 260/413; 260/414; 252/369; 252/370
[58] Field of Search ............... 260/413 R, 413 S, 414; 252/369, 370

[56] References Cited

U.S. PATENT DOCUMENTS

| | | | |
|---|---|---|---|
| 2,190,591 | 2/1940 | Clayton | 252/370 |
| 2,890,232 | 6/1959 | Rogers | 260/414 |
| 3,476,786 | 11/1969 | Lally | 260/413 |
| 3,803,188 | 4/1974 | Scott | 260/413 |

FOREIGN PATENT DOCUMENTS 644431  3/1963  Belgium .

*Primary Examiner*—John F. Niebling
*Attorney, Agent, or Firm*—Bryant W. Brennan; Harold R. Beck

[57] ABSTRACT

Metallic salts of higher molecular weight fatty acids are produced in a continuous process by feeding fatty acid and base into a plug flow reactor to maintain a residence time of about 2 to about 60 minutes at a temperature of about 75° F. to about 280° F. to obtain a metallic salt, then grinding the metallic salt in a hammer mill to obtain coarse particles and then grinding the coarse particles in a jet mill to obtain fine particles of the metallic salt. Optionally, the fatty acid and base may be fed initially into a stirred-tank reactor to maintain a residence time of about 10 to about 80 minutes at a temperature of from about 115° F. to about 300° F. to initiate metallic salt reaction before feeding the metallic salt reaction mixture into the plug flow reactor.

6 Claims, 1 Drawing Figure

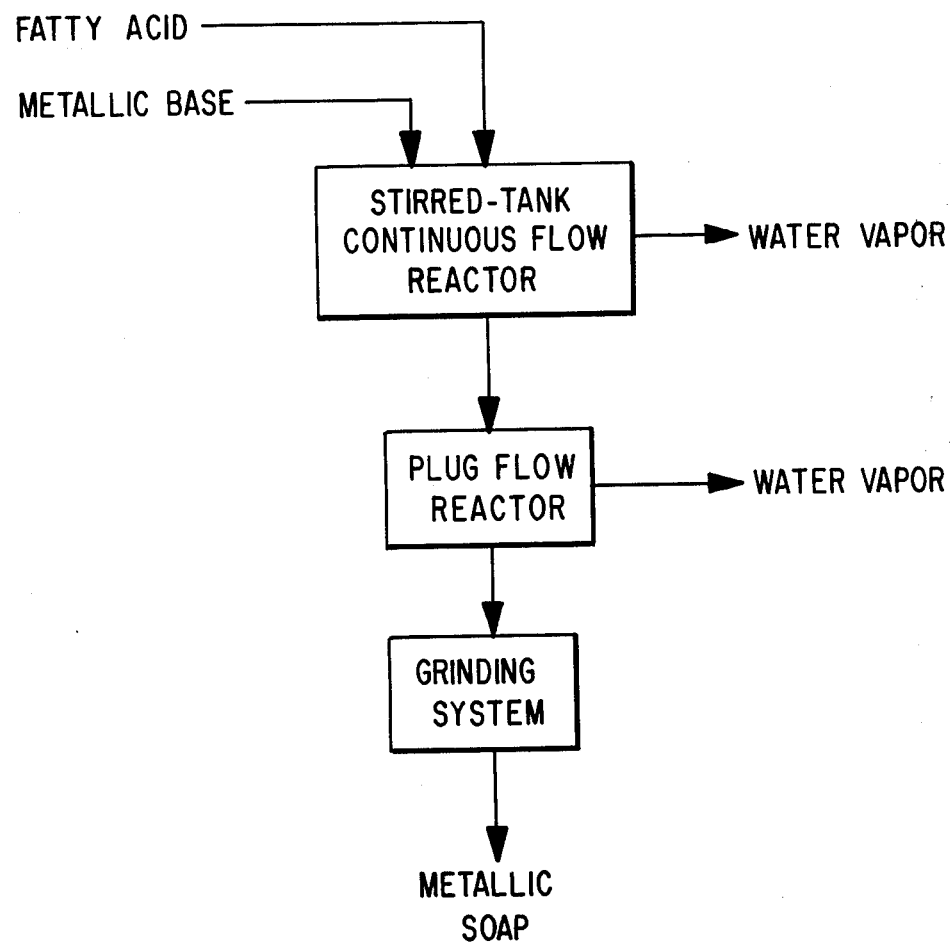

CONTINUOUS PROCESS FOR PREPARING DRY METALLIC SALTS OF HIGHER FATTY ACIDS

This is a continuation of application Ser. No. 028,009, filed Apr. 9, 1979, abandoned.

BACKGROUND OF THE INVENTION

1. Field of the Invention

This invention relates to a continuous process for producing dry water insoluble metallic salts of higher fatty acids and more particularly to a continuous process employing blends of fatty acids, particularly mixtures of stearic and palmitic acids and bases such as zinc oxide or calcium hydroxide to prepare zinc or calcium salts.

2. Description of the Prior Art

Metallic salts of higher molecular weight fatty acids are commercially known as metallic soaps. Metallic soaps which are blends of principally stearic acid, also known as octadecanoic acid, and palmitic acid, also known as hexadecanoic acid, are offered commercially as metallic stearates. The major metallic stearates are calcium, zinc, aluminum and magnesium stearates. Barium, lead, copper, iron, silver and strontium stearates are of less commercial importance.

For many years, dry calcium stearate and zinc stearate have been used as internal lubricants in plastics, mold release agents for rubber, external lubricants for wire drawing and metal working, sanding sealers, flatting agents for varnishes and lacquers, cosmetic emulsifiers and aerosol dispensing aids. Aqueous dispersions of calcium and zinc stearates have also been used as paper coatings, dip coating for uncured rubber slabs or extrusions, waterproofing agent for cement, mold release and antitack agent for stored slabs, sheets and extruded articles.

There are numerous processes for the manufacture of calcium stearate, but these are batch operations based on wet fusion, dry fusion and precipitation processes. Zinc stearate is also produced by the wet fusion and precipitation processes.

The wet fusion process uses stearic acid and zinc oxide for zinc stearate or calcium hydroxide for calcium stearate. In this process, a heated batch reaction is carried out in an aqueous media containing an emulsifying agent. Stearates produced by the wet fusion process are used as 40–60% solids aqueous dispersions. This process reaction requires about two hours for completion and further processing is often required to produce uniform dispersions.

Dry fused calcium stearates are produced by adding stearic acid and calcium hydroxide to a batch reactor and heating. The reaction mass is heated to its melting point and maintained in a molten condition until reaction is complete. The batch is then cooled to solidify in order to permit its crushing and grinding to obtain the desired particle size. Stearates produced by the dry fusion process are characterized by their yellow color and dense particle. Because of these properties, use of dry fusion process stearates is restricted to the wire drawing and metal working industries.

Precipitated zinc and calcium stearates are characterized by their purity, white color, very fine particle size and low bulk density. The precipitation process involves:

(a) A batch saponification reaction employing sodium hydroxide and a fatty acid to produce an aqueous solution of sodium stearate.

(b) A batch precipitation reaction wherein calcium chloride (for calcium stearate) solution or zinc sulfate (for zinc stearate) solution is added to an aqueous solution of the sodium stearate. Insoluble zinc or calcium stearate precipitates out of the aqueous solution which contains sodium chloride or sulfate and some excess calcium chloride or zinc sulfate and forms a slurry.

(c) Filtration and washing of the slurry is required to separate the solid stearate as a filter cake from the salt solution. The number of washings and subsequent filtrations required for the separation is determined by the desired finished product purity. Presence of electrolytic salts in the stearate is undesirable in certain applications, e.g., plastic used in electric wire coating or tape.

(d) After the final filtration, the filter cake is dried in ovens or fluid air driers or similar equipment.

(e) Final grinding to obtain the desired particle size is usually accomplished in hammer mills and/or jet mills.

The precipitation process has a number of disadvantages:

(a) Waste water effluent from the filtration and washing steps must be treated before recycling or discharging into waterways. Zinc wastes are particularly objectionable due to their toxicity to aquatic life and degree of difficulty to adequately treat with standard practices, e.g., settling, neutralization, aeration and biodegradation.

(b) Drying the washed filter cake is a high energy consumption unit operation.

(c) It is not practical to reduce the soluble salt content of the finished product to zero.

(d) The number of unit operations in the precipitation process requires high labor input as well as numerous control devices both of which add to the cost and difficulty in quality control.

The following patents are representative of the prior art on dry metallic soap processes.

Begium Pat. No. 644,431—Unilever, describes the production of dry metallic soaps wherein powdered stearic acid and powdered calcium hydroxide were mixed and charged into a laboratory soap press whose extrusion orifice was a perforated plate. After a number of revolutions of the extrusion screw, temperature of the mixture resulting from the compression in the milling in the front part of the extrusion chamber rose suddenly and the saponification product exuded from the press through the plate in the form of vermicelli which cooled rapidly to form a hard, nonfragile product.

U.S. Pat. No. 2,890,232—Rogers, Jr., et al, issued June 9, 1959, describes a batch process wherein stearic acid and calcium oxide were mixed and heated at 200° F.; water was then added to the reaction mixture. Saponification began at 215° F. and was complete at 310° F. The reaction was rapid.

U.S. Pat. No. 3,476,786—Lally et al, issued Nov. 4, 1969, describes a process wherein finely divided water insoluble metallic salts of higher fatty acids were produced by grinding solid fatty acids with a base such as metal oxides, metal hydroxides or mixtures thereof in the presence of a catalyst and in the absence of water. One example employed solid calcium hydroxide and solid stearic acid in the presence of ammonium carbonate as the catalyst.

There is a definite need for a continuous process for preparing dry metallic salts of higher fatty acids.

SUMMARY OF THE INVENTION

Metallic salts of higher molecular weight fatty acids are produced in a continuous process by feeding the desired fatty acid such as stearic acid and a base such as zinc oxide or calcium hydroxide into a plug flow reactor at an effective rate to maintain a residence time in the reactor of from about 2 to about 60 minutes at a temperature of from about 75° F. to about 280° F. to obtain a metallic salt, then discharging the metallic salt from the plug flow reactor continuously, thereafter feeding the discharged metallic salts from the plug flow reactor into a hammer mill, then grinding the metallic salt in the hammer mill to obtain the salt in form of coarse particles, thereafter feeding the coarse particles from the hammer mill to a jet mill and grinding the coarse particles in the jet mill to obtain the salt in form of fine particles. Optionally, the fatty acid and base may be fed into a stirred-tank reactor at an effective rate to maintain a residence time in the stirred-tank reactor of from about 10 minutes to about 80 minutes at a temperature of about 115° F. to about 300° F. to initiate metallic salt reaction before feeding the metallic salt reaction mixture into the plug flow reactor.

If desired, a catalytic amount of catalyst such as water, a nonionic emulsifier or caustic solution can be added to accelerate reaction.

BRIEF DESCRIPTION OF THE DRAWING

The drawing is a flowsheet showing a system wherein the continuous process of the present invention can be operated.

DESCRIPTION OF THE PREFERRED EMBODIMENTS

The reactants in this continuous process can be added as solids, separately or premixed, or the fatty acid can be in a molten state and added separately. If desired, a catalytic amount of a catalyst can be added as a separate feed to the reactor. Useful catalysts include: water, nonionics, e.g., 6 moles ethoxylated tridecanol either in aqueous solution or concentrated, sodium or potassium hydroxide solution, ammonium carbonate solution.

The reactants can be added to a stirred-tank reactor maintained at a temperature from about 115° to about 300° F. as two separate feeds, i.e., (1) fatty acid, solid flakes or molten, (2) calcium hydroxide or zinc oxide and (3) if desired, 1–2% of catalyst. The feeds should be at rates which give a residence time of from about 10 to about 80 minutes in the stirred-tank reactor for about 0.5 to about 1.0 moles of metallic oxide or hydroxide per mole of fatty acid. The liquid reaction products are removed continuously from the stirred-tank reactor and fed into the plug flow reactor maintained at a temperature from about 75° F. to about 280° F. The residence time in the plug flow reactor is from about 2 minutes to about 60 minutes. If desired, the entire process can be carried out in the plug flow reactor.

Solid reaction products are continuously discharged from the plug flow reactor and fed to a hammer mill to obtain a coarse powder product. The coarse powder product discharge from the hammer mill is fed mechanically to a jet mill in order to obtain the final particle size, less than 0.1% retention on 325 mesh, and bulk density, 40/35 to 70/60 cc per 10 g. Feed rate to the jet mill is adjusted to obtain the desired results.

The fatty acid used in the invention can be either saturated or unsaturated acid having a carbon chain of from about 10 to 22 carbon atoms with carbon chains of about 14 to about 18 carbon atoms being preferred as well as a mixture of two or more of these acids. If desired, the acids may be substituted or unsubstituted. Functional groups which may be present in the acid include hydroxy, chlorine, bromine, etc. Acids which can be utilized in this invention include lauric acid, myristic acid, behenic acid, oleic acid, palmitic acid, stearic acid, ricinoleic acid, hydrogenated tallow fatty acids, hydroxy stearic acid, the fatty acids of hydrogenated castor oil, erucic acid, coconut oil fatty acids, etc. and mixtures of these with each other or with acids such as 9,10 oxylauric acid, 9,10 oxystearic acid, chloromethoxy stearic acid, 9,10 diketo stearic acid, pehnyl stearic acid, etc. or palmitolic acid, stearolic acid, behenolic acids, etc. Such acids are well known articles of commerce and are frequently used in the form of mixtures such as commercial stearic acid, lauric acid or the like. Commercial acids are mixtures of saturated and unsaturated fatty acids of varying carbon chains.

Metal soaps produced by the present invention include those of polyvalent metals, particularly divalent metals such as calcium, magnesium, lead, barium, strontium, zinc, iron, cadmium, nickel, copper, tin and mixtures of the above. The solid metallic component which is reacted with the fatty acid to form metal soaps in accordance with this invention can be either the metallic oxides, metallic hydroxides or metal carbonates or may be mixtures of the above. Typical metallic compounds which may be utilized to produce the metallic fatty acid soap in accordance with this invention include cadmium oxide, zinc carbonate, ferrous oxide, cadmium carbonate, calcium carbonate, calcium hydroxide, lead oxide, lead hydroxide, magnesium oxide, magnesium carbonate, cadmium hydroxide, zinc oxide, barium hydroxide, zinc hydroxide, etc.

The present invention provides a continuous process for the manufacture of dry metallic stearates. Further, the improved process of this invention eliminates: (1) waste water effluent, high energy consumption, complexity of operation and residual soluble impurities inherent in the precipitation process, (2) high density and dark color of the batch dry fusion process. This invention also provides a continuous process for the manufacture of dry metallic stearates using various catalysts to accelerate the reaction. The invention also provides a method by which bulk density of metallic stearates can be varied.

In this invention from about 0.5 to about 1.0 moles of zinc oxide or calcium hydroxide per mole of fatty acid can be added at such rates to a reaction system maintained at temperatures of from about 115° to 280° F. so that reaction occurs over a reaction time of from about 10 to about 80 minutes and the reaction products are removed continuously from the reaction system thereafter processed continuously to obtain the desired particle size and bulk density. If desired, the reaction can be accelerated by addition of a catalytic amount of a catalyst.

The stirred-tank reactor can be a standard vertical, dished bottom tank designed for atmospheric or low pressure service equipped for heating and cooling with coils or jacket for a temperature range of 60° to 300° F. The vessel should be of a suitable material of construction such as 304 stainless steel. It should be equipped with baffles, an agitator, top feed nozzles and a bottom discharge. A level control device on the discharge is also required, e.g., a level control valve.

Reaction vessels of different design can easily be adapted to this process.

The plug flow reactor can be almost any elongated system capable of heat transfer and/or shear energy generation and continuously moving material of a consistency that may vary from a viscous liquid to a paste to a solid. Examples of such equipment would be a jacketed screw conveyor or an extruder. The equipment used in the examples cited was a Baker Perkins M-P Mixer.

The M-P is a twin screw, self-wiping, continuous mixer equipped with a jacket and variable speed drive. The internals of the M-P consisted of two 4 inch I.D. interlocking barrels with an overall height of 7.1 inches. Contained in the barrel was a twin screw divided into three sections: (1) 8.5 inch feed section with interlocking helical screws, (2) 23.5 inch mixing section with lens-shaped cross-section paddles, and (3) 4 inch discharge section similar to the feed section. The mixing section paddles were 4 inches long with an axis perpendicular to the adjorning paddle. The free volume of the barrel chamber was 0.23 cubic feet. Various feed and discharge mechanisms can be used with the unit.

The hammer mill can be of standard design for pulverizing soft solids. Other grinding equipment can also be used. The equipment used in the examples cited was a Pulverizing Machinery Mikro-Pulverizer—Bantam Model.

The unit had a horizontal rotor shaft with T-shaped hammers. The rotor (5 inch diameter) ran at a constant speed (16,000 rpm) in a cylindrical housing containing grinding plates. The clearance between the grinding plates and hammers was constant as was the number of hammers and the size of the discharge opening. The discharge opening was equipped with a removable screen, cylindrically shaped covering the bottom half of the housing. Material was fed by gravity into a hopper containing a lump breaker at the bottom. Material passed down into a feed screw leading to the grinding chamber. The unit also had a dust collection bag.

The Mikro-Pulverizer and other commercial units can be equipped with an air classifying system to obtain a finer particle size. The equipment used to obtain the desired fine particle size in the examples cited was a Reduction Engineering jet mill.

The jet mill was a 2 inch model requiring 210 scfm and 100 psi. The unit employs a hollow elongated torus (donut shaped) placed vertically. Material was fed by gravity into a hopper which discharges into the end of a venturi feed throat. Material was drawn through the venturi into the outer periphery of the base of the unit where high velocity streams of air were introduced at the periphery. The jet stream carrying the particles flowed up the tube into a classification section. Fines and spent air exit the unit through an opening on the inside wall. Oversized particles were recycled down the tube into the base. Fines were collected with a dust bag.

There are many other suitable commercial units operating with fluid-energy used as the grinding medium.

In the examples below, the free fatty acid content of metallic salts is determined by weighing a 2 g sample of solid metal soap in a 250 ml beaker and adding 100 g of ethanol to the beaker to extract the unreacted fatty acid from the metal soap. After 10 minutes of stirring, the mixture in the beaker becomes a two phase system, i.e., a solid metal soap phase and a liquid ethanol phase containing dissolved unreacted fatty acid. The liquid ethanol phase is separated from the solid metal soap phase by filtration. After filtration, the free fatty acid content in the ethanol phase is determined by titrating to a pH of about 7 with 0.05 N sodium hydroxide. The free acid content is determined and reported as if the free acid dissolved in the ethanol phase is stearic acid. The percent free fatty acid (%FFA) is the percentage of free acid remaining in the soap after reaction. The lower the percent free fatty acid the more complete the reaction between the free acid and base.

For a fuller understanding of the nature of this invention, reference may be made to the following examples which are given merely to illustrate the invention and are not to be construed in a limiting sense. All weights, proportions and percentages are on a weight basis unless otherwise indicated. Likewise, all temperatures are °F. unless otherwise indicated. In the tables, ranges are shown as 1/2 rather than 1-2.

EXAMPLE I

This example illustrates the continuous process of the present invention using 1.0 mole of zinc oxide and 1.7 moles of a fatty acid blend containing 50% palmitic, 35% stearic, 10% unsaturated, 5% C-14, C-15, C-17 saturated fatty acids to produce a zinc soap.

The zinc oxide (17.6 lbs) and fatty acid blend (100.0 lb) were mixed at room temperature in a ribbon blender to obtain a uniform mix. The mix was fed mechanically at a rate of 0.6 lb/min into a continuous-flow stirred-tank reactor. The reactor was an 8 gallon, open top, stainless steel tank with a 12 inch diameter and dished bottom equipped with coils, 3 equally spaced flat baffles and an 8 inch high internal overflow well for discharge. Agitation was provided with a ¼ horsepower drive and a single 5 inch diameter propeller type impeller set ½ inch from the bottom of the tank.

The internal overflow well controlled the reaction mass volume to 0.52 cubic feet thereby providing a residence time of about 45 minutes. Temperature of the reaction mass was maintained at 245°–250° F. by controlling the steam inlet pressure to the coils to provide a steam temperature of 273°–280° F. The free fatty acid content of the reaction mass was 2.0–6.1%.

The liquid reaction mass continuously overflowed into the well and discharged by gravity into the plug flow reactor. The Baker-Perkins M-P Mixer, previously described, was used with a discharge orifice to restrict the flow of the reaction products. The orifice provided an annular opening about ⅛ inch wide over a 2 inch diameter with the end of the upper drive shaft protruding through the orifice hole. The twin screw, self-wiping agitator shaft was operated at 28 ppm. Jacket temperature was maintained at 216° F. by regulating the inlet steam pressure. Residence time was approximately 10–15 minutes. Solid flaked reaction mass was continuously discharged into a surge vessel at a temperature of 220°–222° F. with a free fatty acid content of 0.3–0.7%.

The solid flakes were fed by hand into a hammer mill without a classifying screen and discharged at 70° F. in the form of a coarse powder. The hammer mill is the unit described above.

The coarse powder was fed mechanically to a 2 inch diameter jet mill operated at 100 psi. Feed rates were varied from 0.2 to 2 lbs/min. The jet mill is the unit described above.

Analysis of the finished product showed the following as compared to typical precipitated zinc stearate:

|  | Example I | Typical Precipitated Product |
|---|---|---|
| Ash, % | 15.1 | 14.0–15.8 |
| FFA, % | 0.2 | 0.5 |
| Fineness, % + 325 mesh | 0.1 | 0.1 |
| Bulk, cc/10 g | 51/42 | 70/60–120/110 |
| Moisture | 0.2 | 0.3–0.5 |

The ash content (% Ash) can be varied with the amount of zinc oxide used in the initial mix. This example used the zinc oxide charge necessary to obtain a medium ash content product. It should also be noted that the typical precipitated ash content shown includes 0.3% soluble ash. Soluble ash content in precipitated products originated from the unwashed sodium and zinc sulfates. Example I ash content was 100% insoluble, that is, no residual salts are present.

Percent free fatty acid (%FFA) is a measure of completeness of reaction. A theoretical value 0% FFA is possible but %FFA less than 0.5% is acceptable in the industry.

Fineness was measured in terms of retention on 325 mesh screen. Bulk, the inverse of bulk density, was measured as volume in cubic centimeters per 10 g. The first number in the ratio represents the initial volume and the second number in the ratio volume after the graduated cylinder containing the 10 g of the finished powder was tapped 60 times.

EXAMPLE II

This example is similar to Example I except a catalytic amount of water was used and only the reaction phase of the process was evaluated.

The zinc oxide (17.6 lb) and fatty acid blend (100.0 lb) were mixed at room temperature in a ribbon blender to obtain a uniform mix. The mix was fed mechanically at a rate of 0.6 lb/min into the continuous flow stirred-tank reactor. Concurrently, 2 ml/min (0.75% of total feed) of water was fed to the reactor. The reactor was the same as in Example I except 4 equally spaced baffles and a 4 inch diameter turbine type impeller were used. As in Example I the residence time was about 45 minutes. The temperature of the reaction mass was maintained at 240° F. by controlling the steam inlet pressure to the coils to provide a steam temperature of 258° F. The free fatty acid content of the reaction mass was 27.0–30.0%.

The liquid reaction mass was fed to the Baker-Perkins M-P Mixer as in Example I. The jacket temperature was maintained at 220°–222° F. and agitator shaft speed set at 42 rpm. The residence time was approximately 10–15 minutes. The solid flaked reaction mass was continuously discharged at 208° F. and a free fatty acid of 0.3%.

EXAMPLE III

This example is similar to Example II except the residence time in both reactors were reduced.

The zinc oxide/fatty acid blend were mixed as in Examples I and II. The mix was fed mechanically at a rate of 1.1 lb/min into the continuous flow stirred-tank reactor. Cocurrently, 3.6 ml/min (0.72% of total feed) of water was fed to the reactor. The reactor was the same as in Example II. The feed rate of 1.1 lb/min provided a residence time of about 22 minutes. The temperature of the reaction mass was maintained at 239°–242° F. by regulating the steam temperature 270°–273° F. in the coils. The free fatty acid content of the reaction mass was 46.5–50.0.

The liquid reaction mass was fed to the Baker-Perkins M-P Mixer as in Example II. The jacket temperature was maintained at 214°–215° F. and the agitator shaft speed was varied from 85 to 57 rpm during the experiment. The residence time was about 5–10 minutes. A viscous liquid reaction mass was continuously discharged at 210°–220° F. and a free fatty acid of 23.6–38.4%.

EXAMPLE IV

This example is similar to Example I except the residence time in the continuous flow stirred-tank reactor was reduced and only the reaction phase of the process was evaluated.

The zinc oxide/fatty acid blend were mixed as in Example I. The mix was fed mechanically at a rate of about 0.6 lb/min into the stirred-tank reactor. The reactor was the same as in Example I except 2 equally spaced baffles and a 6 inch high internal overflow well were used. The residence time was about 31 minutes. The reaction mass temperature was maintained at 267°–270° F. by controlling the steam inlet temperature to 297°–300° F. in the coils. The free fatty acid content of the reaction mass was 7.4–28.3%.

The liquid reaction mass was fed to the Baker-Perkins M-P Mixer as in Example I. The jacket temperature was maintained at 221°–222° F. and the agitator shaft speed was varied from 42 to 57 rpm during the experiment. The residence time was about 10–15 minutes. At the low speed, 42 rpm, a solid reaction mass was discharged at 183°–210° F. and a 0.3–11.5% free fatty acid. At 57 rpm, the discharge changed to a paste at 225°–228° F. and an 18.9% free fatty acid.

TABLE I

| SUMMARY OF EXAMPLES I–IV | | | | |
|---|---|---|---|---|
| Example | I | II | III | IV |
| Run number | 233 | 243 | 245 | 231 |
| Moles fatty acid/ZnO | 1.7 | 1.7 | 1.7 | 1.7 |
| Feed rate, lb/min | 0.6 | 0.6 | 1.1 | .6 |
| Catalyst, ml/min |  | 2.0 | 3.6 |  |
| Stirred tank reactor | | | | |
| Coil temp., °F. | 273/280 | 258 | 270/273 | 297/300 |
| Reactant temp., °F. | 245/250 | 240 | 239/242 | 267/270 |
| Residence time, min | 45 | 45 | 22 | 31 |
| % FFA | 2.0/6.1 | 27.0/30.3 | 46.5/50.0 | 7.4/28.3 |
| M-P | | | | |
| Jacket temp., °F. | 216 | 220/222 | 214/215 | 221/222 |
| Discharge temp., °F. | 220/222 | 208 | 210/220 | 159/228 |
| Speed, rpm | 28 | 42 | 85/57 | 42/57 |
| Residence time, min | 10/15 | 10/15 | 5/10 | 10/15 |
| % FFA | 0.3/0.7 | 0.3 | 23.6/38.4 | 0.3/18.9 |

EXAMPLE V

This example illustrates the continuous process of the present invention using 1.0 moles calcium hydroxide and 2.0 moles of a fatty acid blend containing 28% palmitic, 65% stearic, 2% unsaturated, 5% C14, C15, C17 saturated fatty acids to produce a calcium soap.

The calcium hydroxide (13.7 lbs) and fatty acid (98.9 lbs) were mixed in a ribbon blender to obtain a uniform mix. The mix was fed mechanically at a rate of 1.6 lb/min into a plug flow reactor.

The Baker-Perkins M-P Mixer, described in Example I, was operated at 177 rpm. Jacket temperature was maintained at 115° F. by regulating the inlet steam pressure. Residence time was about 5–8 minutes. The reaction mass was continuously discharged at a temperature of 133°-138° F. with a free fatty acid content of 5.4-8.8% into a 5 gallon pail. The reaction product was fed by hand into a hammer mill without a classifying screen and discharged into another 5 gallon pail in the form of a coarse powder at a temperature of 60° F.

The coarse powder was fed to a 2 inch diameter jet mill operated at 100 psi.

Analysis of the finished product showed the following as compared to typical precipitated calcium stearates:

|  | Example V | Typical Precipitated Product |
|---|---|---|
| Ash, % | 10.5 | 9.7-12.3 |
| FFA, % | 0.2 | 0.1-0.4 |
| Fineness, % + 325 mesh | 0.1 | 0.05-2.5 |
| Bulk, cc/10 g | 40/36 | 45/35-100/90 |
| Moisture | 2.6 | 1.5-2.5 |

EXAMPLES VI-X

These examples are similar to Example V except the fatty acid blend/calcium hydroxide mole ratio was reduced, the fatty acid blend contained more palmitic and only the reaction phase of the process was evaluated.

In each of these examples, 1.0 moles of calcium hydroxide and 1.9 moles of a fatty acid blend containing 50% palmitic, 35% stearic, 10% unsaturated, 5% C-14, C-15, C-17 saturated fatty acids were used to produce a calcium soap.

The calcium hydroxide (31 lb) and fatty acid blend (200 lb) were mixed and mechanically fed to the Baker-Perkins M-P Mixer as in Example V. The feed rate, jacket temperature and twin-screw speed were changed in each example resulting in the following:

TABLE II

| | SUMMARY OF EXAMPLES VI-X | | | | |
|---|---|---|---|---|---|
| Example number | VI | VII | VIII | IX | X |
| Run number | 91 | 95 | 99 | 111 | 117 |
| Feed rate, lb/min | 5.0 | 1.7 | 1.7 | 1.7 | 0.3 |
| Jacket temp., °F. | 213/217 | 78/79 | 250 | 115 | 113/119 |
| Speed, rpm | 220 | 118 | 118 | 28 | 177 |
| Residence time, min | ½ | 5/7 | 5/7 | 5/7 | 25/35 |
| Discharge temp., °F. | 153/173 | 117/120 | 208/211 | 118/119 | 113/118 |
| Free fatty acid, % | 24.3/33.0 | 19.5/27.0 | 19.5/25.0 | 12.8/16.2 | 14.8/22.2 |

EXAMPLE XI

This example is similar to Examples V-X except a zinc soap was made using a catalyst and 1.0 moles of zinc oxide and 1.7 moles of a fatty blend similar to the one used in Examples I-IV, VI-X.

The zinc oxide (22.5 lb) and fatty acid (150 lb) were mixed as in all previous examples and mechanically fed at a rate of 0.3 lb/min to the Baker-Perkins M-P Mixer. Cocurrently, a catalyst containing 0.76% sodium hydroxide and 0.15% ethoxylated tridecyl alcohol aqueous solution was added at a rate of 9.2 ml/min (6.1% of the total feed).

The M-P was operated at 28 rpm and equipped with an overflow weir discharge mechanism that covered 80% of the barrel chamber cross-section. The jacket temperature was maintained at 268°-272° F. by regulating the inlet steam pressure. The residence time was about 55 minutes. The liquid reaction mass was continuously discharged at a temperature of 201-224° F. with a free fatty acid of 20.2-36.4%.

EXAMPLE XII

This example illustrates the continuous process of the present invention wherein the bulk of the finished product was varied by adjusting the feed rate to the jet mill.

A sample of the hammer milled product from Example I was mechanically fed to the jet mill at the following rates to obtain the bulks shown for the feed rates shown below:

| lb/min | % + 325 M | cc/10 g |
|---|---|---|
| 0.2 | 0 | 63/54 |
| 1.0 | 0 | 46/40 |
| 2.0 | 42/35 | 42/35 |

The lower feed rate, 0.2 lb/min resulted in a bulk closely approximating the 70/60 bulk of high density precipitated zinc stearate. High density stearates are highly desirable in many applications because of their minimum agglomeration and low dusting properties.

While the invention has been described with reference to certain specific embodiments thereof, it is understood that it is not to be so limited since alterations and changes may be made therein which are within the full and intended scope of the appended claims.

We claim:

1. A continuous process for producing a metallic salt of a higher fatty acid comprising:
    (a) feeding a higher fatty acid and a base at an effective rate to a stirred-tank reactor to maintain a liquid state with a residence time in the stirred-tank reactor of from about 10 to about 80 minutes and a temperature of from about 115° F. to about 300° F. to initiate metallic salt reaction, then
    (b) discharging the liquid metallic salt from the stirred-tank reactor, thereafter
    (c) feeding the liquid metallic salt into a plug flow reactor at an effective rate to maintain a residence time in the reactor of from about 2 to about 60 minutes and a temperature of about 75° F. to about 280° F. to complete metallic salt reaction and obtain a solid metallic salt, then
    (d) discharging the solid metallic salt from the plug flow reactor, thereafter
    (e) feeding the solid metallic salt into a hammer mill, then
    (f) grinding the metallic salt in the hammer mill to obtain the salt in form of coarse particles, thereafter
    (g) feeding the coarse particles to a jet mill, and then
    (h) grinding the coarse particles in the jet mill to obtain the salt in form of fine particles.

2. The process of claim 1 wherein a mixture of the fatty acid and base is fed into the plug flow reactor at an effective rate to maintain a residence time in the plug flow reactor of from about 2 minutes to about 60 minutes and a temperature of about 75° F. to about 280° F. so that the reaction mixture is in liquid state at the feed end of the reactor and forms a solid metallic salt at the discharge end of the reactor.

3. The process of claim 1 wherein the base is zinc oxide.

4. The process of claim 1 wherein the base is calcium hydroxide.

5. The process of claim 1 wherein the higher fatty acid contains about 10 to about 22 carbon atoms.

6. The process of claim 1 wherein the higher fatty acid contins about 14 to about 18 carbon atoms.

* * * * *